United States Patent [19]

Claus

[11] Patent Number: 5,136,100
[45] Date of Patent: Aug. 4, 1992

[54] PROCESS FOR PRODUCING 3-METHYL-2-PENTYL-CYCLOPENT-2-EN-1-ONE

[75] Inventor: Harald Claus, Haltern, Fed. Rep. of Germany

[73] Assignee: Huls Aktiengesellschaft, Marl, Fed. Rep. of Germany

[21] Appl. No.: 436,625

[22] Filed: Nov. 15, 1989

[30] Foreign Application Priority Data

Jan. 13, 1989 [DE] Fed. Rep. of Germany ....... 3900815

[51] Int. Cl.$^5$ .............................................. C07C 45/00
[52] U.S. Cl. ...................................................... 568/354
[58] Field of Search ........................................ 568/354

[56] References Cited

U.S. PATENT DOCUMENTS 3,953,514  4/1976  Yamazaki .................. 568/354

FOREIGN PATENT DOCUMENTS 58-162548   9/1983  Japan ...................... 568/354
58-170728  10/1983  Japan ...................... 568/354
58-208247  12/1983  Japan ...................... 568/354
894638      4/1962  United Kingdom ........... 568/354

OTHER PUBLICATIONS

Rai et al, J. Ind. Chem. Soc., vol. 34, p. 178 (1975).
Eaton et al, J. Org. Chem., vol. 38, p. 4071 (1973).
Patent Abstracts of Japan, Band 7, No. 285 (C-201) [1430], Dec. 20, 1983.

*Primary Examiner*—James H. Reamer
*Attorney, Agent, or Firm*—Oblon, Spivak, McClelland, Maier & Neustadt

[57] ABSTRACT

A process for producing 3-methyl-2-pentylcyclopent-2-en-1-one by cyclodehydration of γ-methyl-γ-decalatone, which comprises heating γ-methyl-γ-decalactone at a temperature effective for said cyclodehydration in the presence of an effective amount of phosphoric acid as a catalyst, and a mineral oil having a boiling point which is higher than that of said starting material and said product, and removing said product from the reaction mixture.

7 Claims, No Drawings

PROCESS FOR PRODUCING 3-METHYL-2-PENTYL-CYCLOPENT-2-EN-1-ONE

BACKGROUND OF THE INVENTION

1. Field of the Invention

The present invention relates to a process for producing 3-methyl-2-pentyl-cyclopent-2-en 1-one.

2. Description of the Background

Acid cyclodehydration of the readily available alkyl-substituted γ-lactones to form alkylated cyclopent-2-enones has long been known. For example, according to French Pat. 765,515, γ-undecalactone is cyclodehydrated by means of concentrated sulfuric acid to form 2-hexylcyclopent-2-enone. As another example, according to DRP Pat. 639,455, γ-methyl-γ-decalactone (5-hexyl-5-methyl-dihydro-2(3H)-furanone) is cyclodehydrated at 300° C. with silica gel to form 3-methyl (dihydrojasmone). Dihydrojasmone is a known fragrance.

The first process affording high yields was published by C. Rai and S. Dev (J. Indian Chem. Soc. 34, 178 (1957). This process uses polyphosphoric acid in the form of a solid mixture of phosphorus pentoxide and 85% phosphoric acid, but more than 24 mole equivalents are required for complete conversion of the lactone at 97° C. The product is then extracted from the solid polyphosphoric acid. In industrial applications, however, such a process is unusable because of the corrosiveness of hot phosphoric acid melts and also due to problems caused by disposing phosphoric acid waste water contaminated with organic compounds. Thus, this conventional process is plagued by the use of solid phosphoric acid as a cyclodehydration reagent wherein large reagent quantities and long reaction times are required. This process is also attended by corrosion and waste water contamination with organic compounds.

A liquid reagent developed by P. E. Eaton et al. (J. Org. Chem. 38, 4071 (1973) consisting of 10 parts by weight of methanesulfonic acid and 1 part by weight of phosphorous pentoxide also entails considerable technical problems. First, in order to convert γ-methyl-γ-decalactone into dihydrojasmone, about 80 times the amount by weight of this reagent is needed. Second, the mixture is so aggressive that it can only be used at room temperature necessitating the use of long reaction times, such as 33 hours. Third, the extraction of the water-soluble methanesulfonic acid with organic compounds creates contaminated waste water.

German Pat. Discl. 24 39 742 describes, among other things, the cyclodehydration of γ-lactones in solid acids at high temperatures. For example, γ-methyl-γ-decalactone is converted by flash pyrolysis with borophosphate heated to 350° C. to form a mixture containing 84 GC-% dihydrojasmone and 4 GC-% adduct. Although this process uses only 10% by weight of catalyst compared to the lactone, the exchange and disposal of the solid, polyester-attached catalyst is, nonetheless, very cost-intensive in practice.

Thus, a need continues to exist for a process for producing 3-methyl-2-pentyl-cyclopent-2-en-1-one by the cyclodehydration of γ-methyl-γ-decalactone that avoids the above disadvantages.

SUMMARY OF THE INVENTION

Accordingly, it is an object of the present invention to provide a process for producing 3-methyl-2-pentyl-cyclopent-2-en-1-one by the cyclodehydration of γ-methyl-γ-decalactone that avoids the disadvantages of the conventional processes for preparing the same.

The above object and others which will become apparent are provided by a process for producing 3-methyl-2-pentyl-cyclopent-2-en-1-one, which entails heating γ-methyl-γ-decalactone of a temperature effective for said cyclodehydration in the presence of an effective amount of phosphoric acid as a catalyst, and a mineral oil having a boiling point which is higher than that of said starting material and said product, and removing said product from the reaction mixture.

DETAILED DESCRIPTION OF THE PREPARED EMBODIMENTS

The present invention entails a process for producing 3-methyl-2-pentyl-cyclopent-2-en-1-one by catalytic cyclodehydration of 5-hexyl-4-methyldihydro-2(3H)-furanone (γ-methyl-γ-decalactone) in the presence of phosphoric acid at elevated temperatures, wherein the catalyst used is a mixture of from about 5 to 20% by weight of phosphoric acid in mineral oil with a high boiling point and wherein the reaction is carried out at from about 145° to 175° C., the resulting product as well as the reaction water being removed from the reaction mixture by the application of a reduced pressure.

All mineral oils having boiling points higher than the boiling points of the product and starting material may be used. That is, white oils that consist of a mixture of saturated alkanes and cycloalkanes with boiling point ranges of about 350° to 410° C. and about 385° and 485° C., respectively, are used in accordance with the present invention.

The reduced pressure which is used in accordance with the present invention to remove the product from the reaction mixture depends upon the boiling point of the product and the pressure drop in the distillation column.

By using the catalyst of the present invention, excellent yields of 3-methyl-2-pentyl-cyclopent-2-en-1-one can be obtained in a continuous process. The process of the present invention involves adding the lactone in question by drops to the catalyst heated to from about 145° to 175° C., and preferably about 150° to 170° C., and distilling the resulting product at sufficiently low pressure by means of a distillation column of adequate separating capacity, whereupon the reaction water released is generally removed in gas form. The process may, of course, be conducted in batches as well. The phosphoric acid may be used at full strength or in the form of an aqueous solution. For 1 mole of phosphoric acid in the catalyst, the activity of the catalyst remains at the same high level after conversion of 10 moles of lactone. After conversion of 20 moles of lactone, catalyst activity is still 80 to 90% of the starting value.

The process of the present invention offers the following surprising advantages:

1. The catalyst mixture of phosphoric acid and high boiling point mineral oil is in liquid form and is easy to handle, 2. Under the given conditions, there are no corrosion problems for nickel alloys such as Hastalloy B or C, 3. Only catalytic quantities of phosphoric acid are used, 4. The catalyst mixture may be treated without difficulty by adding small quantities of a hydrocarbon solvent and water and separating out the underlying phosphoric acid phase. This regenerated phosphoric acid can be reused without further processing, 5. No waste water contaminated with organic compounds is produced, and 6. Mild reaction conditions and the short time spent in the reaction zone by the resulting product make it possible to obtain high yields of nearly isomer-pure cyclopent-2-enone.

The present invention will now be further illustrated by reference to certain examples which are provided solely for illustration and are not intended to be limitative.

EXAMPLE 1

A 2-L, three-necked flask with an internal thermometer, magnet stirrer, dropping funnel, heatable distillation column (height = 50 cm, inner diameter = 30 mm, $V_4A$-Multifil packing) with reflux distributor, cooler and exchange receiver is charged with 900 g of a white oil with a high boiling point, 100 g (1 mole) of 98% phosphoric acid, and 184.3 g (1 mole) of 5-hexyl-5-methyldihydro-2(3H)-furanone. The column mantel heated to 65° C.; a head pressure of 3 hPa is applied, and the contents of the flask are heated to 160° C. bottom temperature.

With the reflux distributor closed, the resulting low-boiling point elements are allowed to collect in the column for about 3 hours. The reflux distributor is then opened at controlled intervals in a ratio of 10:1, and the resulting products are continuously distilled (head temperature about 90° C.). The resulting reaction water overflows in the form of a gas at this internal pressure and is removed by freezing in a cooling trap.

The quantity of product distilled after 1 hour is replaced each time by adding 1.1 times the quantity of 5-hexyl-5-methyldihydro-2(3H)-furanone, which is added to the reaction bottom via the dropping funnel.

To halt the continuous reaction, the addition of 5-hexyl-5-methyldihydro-2(3H)-furanone is ceased until the stream of product is exhausted, distillation continues, the apparatus is aerated and the bottom is allowed to cool, at least 10% by weight water is added to the bottom and for better phase separation 10 to 20% by weight of a hydrocarbon solvent, such as cyclohexane. The mixture is well agitated at about 60 to 80° C., and the underlying aqueous phosphoric acid phase is separated out and after a determination of content can be reused without further processing in a new run. The organic phase remaining in the reactor is fractionated in order to recover the solvent used and the residues of product and adduct. The remaining white oil phase may be used 2 to 3 more times in a new run. At the end of its life cycle, it can be combusted without problems.

By using 1 mole of phosphoric acid with the present method, it is possible to convert 10 moles of 5-hexyl-5-methyldihydro-2(3H)-furanone into 3-methyl-2-pentyl-cyclopent-2-en-1-one at a constant distillation rate. Not until after conversion of about 20 moles of lactone does the product formation rate decline by 10 to 20%.

The distilled product mixture contains, in addition to 90 to 95% by GC surface of 3-methyl-2-pentyl-cyclopent-2-en-1-one, other low-boiling-point decomposition products and 1 to 2 mole-% (per NMR integration) of the product isomer 2-pentylcyclohex-2-en-1-one. These subsidiary low-boiling components are separated out by distilling the product mixture in the above-described apparatus.

| | |
|---|---|
| Yield after reaction of 10 moles of lactone: | 1,498.1 g (9.01 moles) Δ 90% yield of 3-methyl-2-pentyl-cyclopent-2-en-1-one |
| Yield after reaction of 20 moles of lactone: | 2,893.8 g (17.04 moles) Δ 87% yield of 3-methyl-2-pentyl-cyclopent-2-en-1-one |
| Typical wear rates on Hastalloy-C4 sheet metal: | 0.01–0.02 mm/year |

EXAMPLE 2

The procedure of Example 1 is repeated, except that the amount of 5-hexyl-5-methyldihydro-2-(3H)-furanone added is not a function of the prevailing product distillation rate, but is a constant quantity per unit of time (30 ml/h = 28 g/h with the apparatus described). This method insures more even distillation and bottom column utilization. In addition, instead of a 98% solution, here 115.3 g (1 mole) of an 85% phosphoric acid solution is used.

| | |
|---|---|
| Yield after conversion of 10 moles of lactone: | 1,546.0 g (9.30 moles) Δ 93% yield of 3-methyl-2-pentyl-cyclopent-2-en-1-one |

EXAMPLE 3

The procedure used is as in Example 1, except that only half the quantity of white oil, phosphoric acid and lactone is used at a bottom temperature of 170° C. The lactone is added at a constant rate of 30 ml/h = 28 g/h. Product is distilled at the same rate as in Example 2, despite the half quantities input.

| | |
|---|---|
| Yield after conversion of 5 moles of lactone (Δ 10 eq.): | 1,345.9 g (8.09 moles) Δ 81% yield of 3-methyl-2-pentyl-cyclopent-2-en-1-one |
| Typical wear rates on Hastalloy-C4 sheet metal: | 0.09–0.10 mm/year |

EXAMPLE 4

The procedure of Example 1 is repeated, but with the bottom temperature being at 150° C. The lactone is added continuously by drops at the rate of 15 ml/h = 14 g/h.

| | |
|---|---|
| Yield after conversion of 10 moles of lactone: | 1,498 g (9.01 moles) Δ 90% yield |
| Typical wear rates on Hastalloy-C4 sheet metal: | 0.01–0.02 mm/year |

EXAMPLE 5

The procedure of Example 4 is repeated, except that the mixture of phosphoric acid in white oil used is only 5% by weight with the same input quantity of phosphoric acid. To adjust for the reduced product distillation rate, the lactone is added evenly at a rate of 12 ml/h = 11 g/h.

| | |
|---|---|
| Yield after conversion of 10 moles of lactone: | 1,452.3 g (8.73 moles) Δ 87% yield |
| Typical wear rates | 0.01 mm/year |

EXAMPLE 6

As in Example 4, the lactone is converted using bottom temperature of 150° C., but 100 g (1 mole) of 98% phosphoric acid is used in only 400 g of high-boiling-point white oil (catalyst mixture 20% phosphoric acid by weight). The lactone may be added by drops at a constant rate of 20 ml/h=18.5 g/h.

| Yield after conversion of 10 moles of lactone: | 1,489.9 g (8.96 moles) Δ 90% yield |
| --- | --- |
| Typical wear rates on Hastalloy-C4 sheet metal: | 0.02 mm/year |

The present invention provides a surprisingly advantageous process for the production of 3-methyl-2-pentyl-cyclopent-2-en-1-one. The product is useful as a fragrance in perfumes, for example.

Having now described the present invention, it will be apparent to one skilled in the art that many modifications may be made to the above-disclosed embodiments while remaining within the spirit and scope of the present invention.

What is claimed as new and desired to be secured by Letters Patent is:

1. A continuous process for producing 3-methyl-2-pentyl-cyclopent-2-en-1-one by cyclodehydration of γ-methyl-γ-decalactone, which comprises continuously adding and heating γ-methyl-γ-decalactone at a temperature effective for said cyclodehydration in the presence of a catalytically effective amount of phosphoric acid, and a mineral oil having a boiling point which is higher than that of said starting material and said product; and continuously removing said product and water vapor from the reaction mixture, wherein said phosphoric acid is used in an amount of no more than about 0.1 moles per mole of γ-methyl-γ-decalactone throughout said process.

2. The process of claim 1, wherein a mixture of about 5 to 20% by weight of phosphoric acid in high boiling mineral oil is used.

3. The process of claim 1, wherein said reaction is effected at a temperature of about 145° to 175° C.

4. The process of claim 3, wherein said reaction is effected at a temperature of about 150° to 170° C.

5. The process of claim 1, wherein said phosphoric acid is used at full strength or as an aqueous solution.

6. The process of claim 1, wherein said product is removed from the reaction mixture by distillation at reduced pressure.

7. The process of claim 6, wherein prior to said product removal by distillation at reduced pressure, at least 10% by weight of water is added to the reaction mixture.

* * * * *